US009155850B2

(12) United States Patent
Benson

(10) Patent No.: US 9,155,850 B2
(45) Date of Patent: Oct. 13, 2015

(54) INHALER CANISTER CAP

(71) Applicant: Annette Joyce Benson, West Bloomfield, MI (US)

(72) Inventor: Annette Joyce Benson, West Bloomfield, MI (US)

(*) Notice: Subject to any disclaimer, the term of this patent is extended or adjusted under 35 U.S.C. 154(b) by 182 days.

(21) Appl. No.: 13/832,080

(22) Filed: Mar. 15, 2013

(65) Prior Publication Data

US 2014/0261402 A1 Sep. 18, 2014

(51) Int. Cl.
*A61M 11/00* (2006.01)
*A61M 15/00* (2006.01)
*A61M 15/08* (2006.01)

(52) U.S. Cl.
CPC ............. *A61M 15/009* (2013.01); *A61M 15/08* (2013.01)

(58) Field of Classification Search
USPC ........................................ 128/200.14, 200.23
See application file for complete search history.

(56) References Cited

U.S. PATENT DOCUMENTS

| | | | | |
|---|---|---|---|---|
| 4,906,488 A | * | 3/1990 | Pera | 426/573 |
| 4,969,578 A | * | 11/1990 | Gander et al. | 222/131 |
| 5,060,643 A | * | 10/1991 | Rich et al. | 128/200.23 |
| 6,718,969 B1 | * | 4/2004 | Rubin et al. | 128/200.14 |
| 8,381,719 B1 | * | 2/2013 | Lawrence et al. | 128/200.23 |
| 2004/0084045 A1 | * | 5/2004 | Ziegler et al. | 128/200.23 |
| 2005/0241637 A1 | * | 11/2005 | Westrate | 128/200.23 |
| 2007/0095342 A1 | * | 5/2007 | Olfati et al. | 128/200.23 |
| 2007/0119450 A1 | * | 5/2007 | Wharton et al. | 128/200.23 |
| 2009/0101144 A1 | * | 4/2009 | Gamard et al. | 128/203.15 |
| 2011/0247619 A1 | * | 10/2011 | Formica et al. | 128/204.18 |

* cited by examiner

*Primary Examiner* — Kristen Matter

(57) ABSTRACT

A detachable cap is disclosed for an inhaler apparatus having an inhaler housing and a canister configured to hold a first substance that is aerosolized on demand from the user. The apparatus' canister is engaged with the inhaler housing to convey the aerosolized first substance into the user's mouth via a mouthpiece. The detachable cap includes a cap body having a first end and a second end. The detachable cap also includes an actuation surface arranged at the first end, wherein the actuation surface is configured to be depressed by the user to actuate the canister and aerosolize the first substance. The detachable cap additionally includes a feature arranged at the second end and configured to be engaged with at least one of the inhaler housing and the canister to secure the detachable cap to the inhaler apparatus. An inhaler apparatus having such a detachable cap is also disclosed.

20 Claims, 2 Drawing Sheets

INHALER CANISTER CAP

TECHNICAL FIELD

The present disclosure relates to a cap for a canister employed in an inhaler of the type used to administer a medication into a patient's lungs.

BACKGROUND

An inhaler is a device used for delivering a medication into the body of a patient or user of the device via the user's lungs. Inhalers are frequently used in the treatment of asthma, Chronic Obstructive Pulmonary Disease (COPD), and other respiratory diseases. For example, a medication such as Znamivir (Relenza), which is used to treat influenza, is administered via an inhaler.

Although various types of inhalers, such as dry-powder and nebulizer devices, have been employed for administering medications, a metered-dose inhaler (MDI) is the most common type used today. The MDI is designed for delivering a specific amount of aerosolized medication, typically in the form of a short burst, to the lungs of the user. In an MDI, medication is most commonly stored in a canister containing a propellant. The propellant is pressurized to provide a force for generating an aerosol cloud and is also the medium in which the medication is suspended or dissolved.

Generally, in the MDI the canister is inserted into the MDI housing and engaged with a specially provided orifice that is designed to direct the medication into the MDI's mouthpiece. During operation of the MDI, typically the canister itself is pressed by the user to dispense the medication.

SUMMARY

A detachable cap is disclosed for an inhaler apparatus having an inhaler housing and a canister configured to hold a first substance that is aerosolized on demand from the user. The apparatus' canister is engaged with the inhaler housing to convey the aerosolized first substance into the user's mouth via a mouthpiece. The detachable cap includes a cap body having a first end and a second end. The detachable cap also includes an actuation surface arranged at the first end, wherein the actuation surface is configured to be depressed by the user to thereby apply a force to the canister and aerosolize the first substance. The detachable cap additionally includes a feature arranged at the second end and configured to be engaged with at least one of the inhaler housing and the canister such that the detachable cap is secured to at least one of the inhaler housing and the canister.

An inhaler apparatus having such a detachable cap is also disclosed. Such an inhaler apparatus may be configured as a metered-dose inhaler (MDI).

The apparatus' canister may have an exposed portion that is not covered by the inhaler housing. In such a case the feature may be engaged with the exposed portion by generating a tight fit between the detachable cap and the exposed portion of the canister for securing the cap thereto.

The cap body may define an internal surface. In such a case, the feature may be arranged on the internal surface and fit over the exposed portion of the canister.

The cap body and the feature may be formed from dissimilar materials and combined into a unitary structure. In such a case, the material of the feature may be pliant while the material of the cap body may be substantially rigid.

The feature may be configured as a projection.

The cap body and the feature together may define a monolithic structure formed from a pliant material.

The cap body maybe luminous, i.e., configured to glow in low light conditions.

The cap body may include a first portion arranged at the first end proximate to the actuation surface and a second portion arranged at the second end proximate to the feature. In such a case, the first portion may be configured to remain exposed relative to the inhaler housing when the actuation surface is pressed by the user to dispense the aerosolized first substance. Furthermore, the first portion may be configured to extend into the inhaler housing when the first substance is aerosolized.

The second portion may be characterized by a distinct appearance, having a shape or form of either a fruit, a berry, a cartoon character, or a media character.

The cap body may be impregnated with a second substance.

The first substance may include a medication characterized by a distasteful scent. Furthermore, the second substance may be characterized by a scent configured to counteract the distasteful scent of the first substance.

In the event the detachable cap is secured to the inhaler housing, the detachable cap may include a flexible middle section configured to accommodate relative movement between the canister and the inhaler housing.

The above features and advantages, and other features and advantages of the present disclosure, will be readily apparent from the following detailed description of the embodiment(s) and best mode(s) for carrying out the described invention when taken in connection with the accompanying drawings and appended claims.

DETAILED DESCRIPTION

Figure 1:
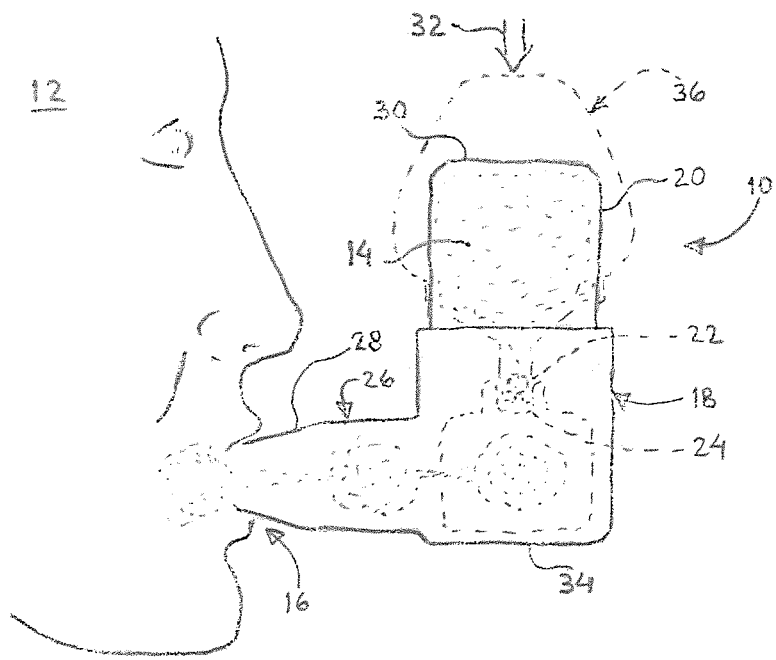
FIG. 1 is a schematic side view of an inhaler apparatus having a detachable cap configured to be depressed for actuating the inhaler apparatus.
Figure 2:
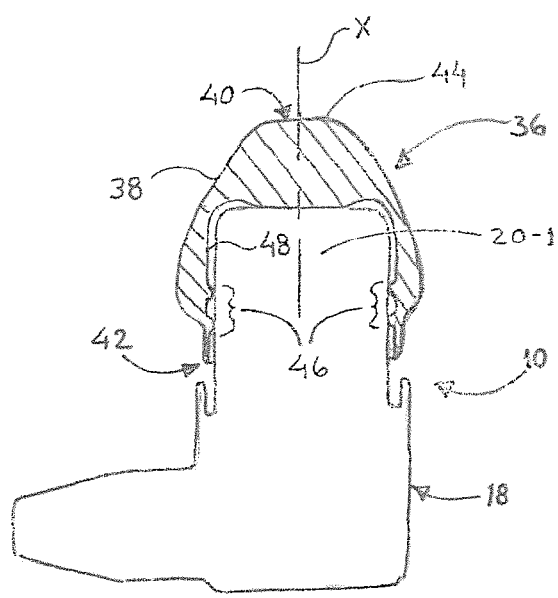
FIG. 2 is a schematic partial cross-sectional side view of the inhaler apparatus shown in FIG. 1, with the detachable cap shown according to one embodiment.

Referring to the drawings, wherein like reference numbers refer to like components, FIG. 1 shows a side view of an inhaler apparatus 10. The inhaler apparatus 10 is employed for delivering a medication into the lungs of a patient or user 12. The inhaler apparatus 10 may be a metered-dose inhaler (MDI), as shown in FIG. 1 that is configured to dispense a predetermined dose or quantity of an aerosolized first substance 14 into the user's lungs via the user's mouth 16.

As shown in FIG. 1, the inhaler apparatus 10 includes an inhaler housing 18. The inhaler housing 18 may be constructed from any appropriate material that is not chemically reactive with the first substance 14, such as moldable plastic. The inhaler apparatus 10 also includes a canister 20 engaged with or inserted into the inhaler housing 18. The canister 20 holds the first substance 14 and includes a metering valve 22 configured to establish the predetermined quantity of the first substance 14 to be aerosolized and dispensed with each actuation of the inhaler apparatus 10. The first substance 14 is pressurized inside the canister 20 and thus facilitates closing of the metering valve 22 following each actuation of the inhaler apparatus 10 by the user 12.

The canister 20 is inserted into a receptacle or orifice 24 that is defined by the structure of the inhaler housing 18 and configured to direct the flow of the first substance 14 toward a specifically contoured mouthpiece 26. As shown, the mouthpiece 26 is in fluid communication with the canister 20 and configured to convey the aerosolized first substance 14 into the user's lungs. Although, the mouthpiece 26 is shown in FIG. 1, the subject mouthpiece may be omitted from the inhaler apparatus 10. When included in the inhaler apparatus 10, the mouthpiece 26 functions as a primary mouthpiece adapted to convey the first substance 14 into the user's mouth 16.

As may be seen in FIG. 1, the mouthpiece 26 includes a discharge nozzle 28 for engagement with the user's mouth 16. The inhaler apparatus 10 may also include a dust cap (not shown) configured to fit over the discharge nozzle 28 in order to prevent contamination of the discharge nozzle while the inhaler apparatus 10 is not in use. The mouthpiece 26 may include a spacer or holding chamber (now shown) disposed downstream of the canister 20 for holding the first substance 14 in aerosolized form prior to the first substance being discharged into the user's mouth 16.

As shown in FIG. 1, to operate the inhaler apparatus 10, the user 12 applies a force 32 to a top portion 30 of the canister 20, while the user's thumb supports a lower portion 34 of the inhaler housing 18. Actuation of the inhaler apparatus 10 typically releases a single metered dose of the first substance 14, which may include a medication and a stabilizing excipient that may be either dissolved or suspended in a volatile propellant. Breakup of such a propellant into droplets, followed by rapid evaporation of those droplets, results in the generation of an aerosolized first substance 14 consisting of micrometer-sized medication particles that may then be inhaled by the user 12. Consequently, in general the inhaler apparatus 10 holds the first substance 14 that is aerosolized for inhalation on demand from the user 12.

With continued reference to FIG. 1, the inhaler apparatus 10 also includes a detachable cap 36. The detachable cap 36 is configured, i.e., designed and constructed, for selective attachment to and detachment from the inhaler housing 18. More specifically, the detachable cap 36 is configured for direct attachment and to thereby be secured to the canister 20. The detachable cap 36 is also configured to enable expedient separation of thereof from the inhaler housing 18. As shown in FIG. 2, the detachable cap 36 includes a cap body 38 having a first end 40 and a second end 42. The detachable cap 36 also includes an actuation surface 44 arranged at the first end 40. During operation of the inhaler apparatus 10, the user 12 presses down on the top portion 30 of the canister 20 via the actuation surface 44 with the force 32. Accordingly, the actuation surface 44 is configured to be engaged, i.e., contacted and depressed, by the user 12 to thereby depress the canister 20 and aerosolize the first substance 14. The actuation surface 44 may have a substantially flat top such that the user's finger(s) may comfortably apply the force 32. The detachable cap 36 additionally includes a feature 46 arranged proximate to the second end 42 and engaged with the canister 20.

As may be seen in FIG. 2, the canister 20 may have an exposed portion 20-1 that is not covered by the inhaler housing 18. The feature 46 is engaged with the exposed portion 20-1 by generating a tight or interference-type fit between the detachable cap 36 and the exposed portion for securing the cap thereto. The cap body 38 defines an inner surface 48. The feature 46 is arranged on the inner surface 48 and fits over the exposed portion 20-1. As shown in FIG. 4, the inner surface 48 may include a convex portion 48-1 configured to facilitate contact between the detachable cap 36 and the exposed portion 20-1 of the canister 20 proximate to a center axis X of the cap body 38. Such contact between the detachable cap 36 and the exposed portion 20-1 at the convex portion 48-1 in turn facilitates direct communication of the force 32 between the detachable cap and the canister 20.

The cap body 38 and the feature 46 may be formed from dissimilar materials and combined into a unitary structure. In such a case, a pliant material may be selected for the feature 46 for secure engagement with the canister 20 and a substantially rigid material may be selected for the cap body 38 providing structural integrity and form retention for the detachable cap 36. In the event that the material of the feature 46 is pliant, the feature will compress against the canister 20 as the detachable cap 36 is pushed onto the canister. Additionally, as the detachable cap 36 is being pushed onto the canister 20, the rigid detachable cap body 38 may provide a suitably robust support for the feature 46. On the other hand, the cap body 38 together with the feature 46 may together define a monolithic structure formed from a pliant material.

The feature 46 may be configured, i.e., designed and formed, as one or more projections, as shown in FIGS. 2-4. Such projections of the feature 46 may be characterized by a height H, as shown in FIG. 3. Additionally, the feature 46 may be a series of such projections interspaced along the inner surface 48 of the cap body 38 such that the projections are concentric with respect to the center axis X of the cap body 38. The feature 46 may be substantially continuous such that projection ring(s) are formed on the inner surface 48, as shown in a cross-sectional view in FIGS. 2 and 4, and in phantom lines in FIG. 3. For example, as may be seen in FIG. 4, the feature 46 may be characterized by a height H, which may be selected based on the durometer of the material, i.e., the measure of material's hardness, selected for the feature. Additionally, the durometer of material for the feature 46 may be selected based on the amount of compression generated by the push-on force required to secure the detachable cap 36 onto the inhaler housing 18. Furthermore, if the feature 46 is configured as a series of projections, such projections may have a graduated or variable height H, as deemed appropriate for secure engagement of the detachable cap 36 to the canister 20. Furthermore, such a series of graduated projections may include a lead projection, i.e., closest to the second end 42, having a smaller height H1 as compared with a height H2 of the projections that follow (shown in FIG. 4).

The cap body 38 may be luminous, i.e., configured to glow in low light conditions. The cap body 38 may include a first portion 38-1 arranged at the first end proximate to the actuation surface and a second portion 38-2 arranged at the second end proximate to the feature 46. The first portion 38-1 is configured to remain exposed relative to the inhaler housing 18 when the actuation surface 44 is pressed by the user 12 to dispense the aerosolized first substance 14. Furthermore, the second portion 38-2 may be configured, i.e., designed and constructed, to extend into the inhaler housing 18 when the first substance 14 is aerosolized. The cap body 38 may be configured to bottom out against the canister 20 to provide a definitive stop for the detachable cap 36 such that there is no remaining space therebetween. The first portion 38-1 may be characterized by a distinct appearance either in the shape or form of a fruit, a berry, a toy, a cartoon character, or a popular media character.

As described above, the first substance 14 may include a medication that is either suspended or dissolved in a propellant. Such medication may be characterized by a distasteful scent, which may make regular administering of the treatment problematic, especially to children. To address the foregoing concern, the detachable cap 36 may be impregnated or saturated with a second substance 50 (shown in FIG. 4) such that the user 12 may sense the second substance during operation of the inhaler apparatus 10. The second substance 50 may be specifically formulated to counteract the distasteful scent and/or flavor of the first substance 14. To such an end, the second substance 50 may be characterized by a pleasing scent or aroma intended to offset, i.e., neutralize, and/or mask, i.e., cover, the distasteful scent of the first substance 14.

Figure 3:
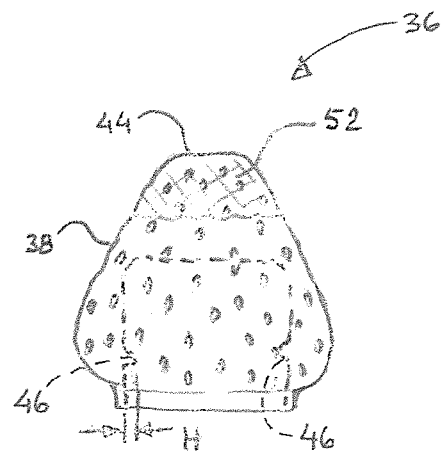
FIG. 3 is a schematic side view of the detachable cap shown in FIGS. 1-2.
Figure 4:
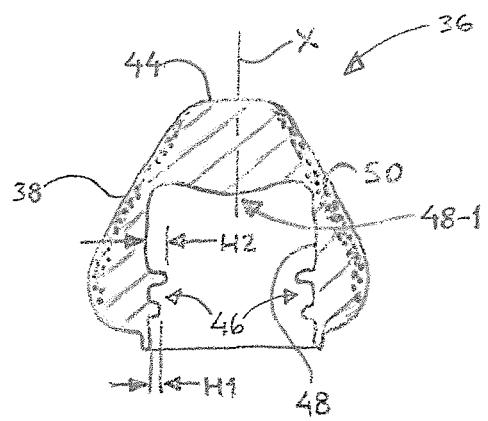
FIG. 4 is a schematic cross-sectional side view of the detachable cap as shown in FIG. 1, according to another embodiment.
Figure 5:
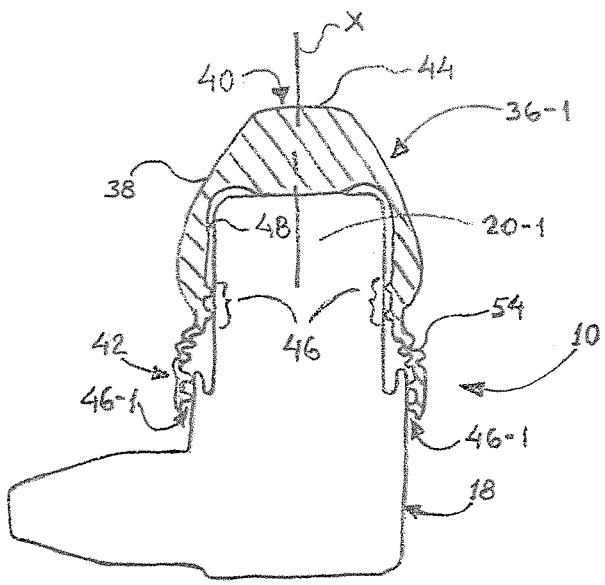
FIG. 5 is a schematic partial cross-sectional side view of the inhaler apparatus shown with the detachable cap according to yet another embodiment.

As shown in FIGS. 4 and 5, the detachable cap 36 may include a portion 52 (shown in FIG. 3) characterized by a distinct, vivid, and/or vibrant tint. The portion 52 may be a localized section on or extend continuously around the cap body 38. Furthermore, the portion 52 may be configured to be luminous, i.e., glow or radiate light, during low or reduced light conditions. The luminous portion 52 may facilitate locating the entire inhaler apparatus 10 or locating the first end 40 of the detachable cap 36 in the dark for actuating the inhaler apparatus 10. Additionally, the distinctly tinted portion 52 may cover the entire cap body 38, as such may be preferred simply for its unique appearance.

FIG. 5 depicts a detachable cap 36-1 according to yet another embodiment. As shown, the detachable cap 36-1 may be configured for direct attachment to the inhaler housing 18. The detachable cap 36-1 may be identical to the detachable cap 36 shown in FIGS. 1-4 in all respects other than having a feature 46-1 arranged proximate to the second end 42 and a flexible middle section 54. The feature 46-1 is engaged directly with the housing 18. As also shown, the detachable cap 36 may also have the feature 46 for additional attachment of the detachable cap 36-1 to the canister 20. As may be seen in FIG. 5, the feature 46-1 is operatively identical to the feature 46. If employed in the detachable cap 36-1, the feature 46 provides secondary attachment to the inhaler apparatus 10, and, as such, may not be absolutely required for operative attachment of the detachable cap 36-1.

As noted above, the detachable cap 36-1 also includes the flexible middle section 54. The flexible middle section 54 is configured to accommodate relative movement between the canister 20 and the inhaler housing 18 during actuation of the inhaler apparatus 10, as the actuation surface 44 is depressed with the force 32 to aerosolize the first substance 14. For example, the flexible middle section 54 may be constructed from a compliant material and/or be configured as a bellows (shown in FIG. 5), i.e., having a flexible, accordion-style construction that permits a distance between the top portion 30 of the canister 20 and the inhaler housing 18 to vary. The detachable cap 36-1 may include a relatively rigid actuation surface 44 and a proximate portion 38-1 of the cap body 38 which is then joined with the flexible middle section 54, or be formed in its entirety from a compliant material used for the flexible middle section.

The detailed description and the drawings or figures are supportive and descriptive of the invention, but the scope of the invention is defined solely by the claims. While some of the best modes and other embodiments for carrying out the claimed invention have been described in detail, various alternative designs and embodiments exist for practicing the invention defined in the appended claims.

The invention claimed is:

1. An inhaler apparatus for dispensing an aerosolized first substance into a user's lungs via the user's mouth, the inhaler apparatus comprising:
   an inhaler housing;
   a mouthpiece in fluid communication with the inhaler housing;
   a canister configured to hold the first substance that is aerosolized on demand from the user, wherein the canister is engaged with the inhaler housing to convey the aerosolized first substance into the user's mouth via the mouthpiece; and
   a detachable cap secured to the inhaler housing and the canister or solely to the canister, the cap including:
   a cap body having a first end and a second end;
   an actuation surface arranged at the first end, wherein the actuation surface is configured to be depressed by the user to thereby apply a force to the canister and aerosolize the first substance; and
   at least one feature arranged at the second end and engaged with the inhaler housing and the canister or solely with the canister;
   wherein:
      the at least one feature secures the detachable cap to the inhaler housing and the canister or solely to the canister via a tight fit to the inhaler housing and the canister or solely to the canister;
      the cap body and the at least one feature are formed from dissimilar materials and combined into a unitary structure; and
      the material of the at least one feature is pliant and the material of the cap body is substantially rigid.

2. The inhaler apparatus according to claim 1, wherein the canister has an exposed portion that is not covered by the inhaler housing, and wherein the at least one feature is engaged with the exposed portion by generating the tight fit between the detachable cap and the exposed portion of the canister for securing the cap thereto.

3. The inhaler apparatus according to claim 2, wherein the cap body defines an internal surface, and wherein the at least one feature is arranged on the internal surface and fits over the exposed portion of the canister.

4. The inhaler apparatus according to claim 1, wherein the at least one feature is configured as a projection.

5. The inhaler apparatus according to claim 1, wherein the cap body is configured to glow in low light conditions.

6. The inhaler apparatus according to claim 1, wherein the cap body includes a first portion arranged at the first end proximate to the actuation surface and a second portion arranged at the second end proximate to the at least one feature, and wherein the first portion is configured to remain exposed relative to the inhaler housing when the actuation surface is pressed by the user to dispense the aerosolized first substance and the second portion is configured to extend into the inhaler housing when the first substance is aerosolized.

7. The inhaler apparatus according to claim 6, wherein the first portion is characterized by a distinct appearance of one of a fruit, a berry, a cartoon character, and a media character.

8. The inhaler apparatus according to claim 1, wherein the cap body is impregnated with a second substance.

9. The inhaler apparatus according to claim 8, wherein:
   the first substance includes a medication characterized by a distasteful scent; and
   the second substance is characterized by a scent configured to counteract the distasteful scent of the first substance.

10. The inhaler apparatus according to claim 9, wherein the detachable cap is secured to the canister and the inhaler housing, and wherein the detachable cap includes a flexible middle section configured to accommodate relative movement between the canister and the inhaler housing.

11. A detachable cap for an inhaler apparatus having an inhaler housing and a canister configured to hold a first substance that is aerosolized on demand from the user, wherein the canister is engaged with the inhaler housing to convey the aerosolized first substance into the user's mouth via a mouthpiece, the detachable cap comprising:
 a cap body having a first end and a second end;
 an actuation surface arranged at the first end, wherein the actuation surface is configured to be depressed by the user to thereby apply a force to the canister and aerosolize the first substance; and
 at least one feature arranged at the second end and configured to be engaged with the inhaler housing and the canister or solely with the canister, such that the detachable cap is secured via a tight fit to of the inhaler housing and the canister or solely to the canister;
 wherein:
  the cap body and the at least one feature are formed from dissimilar materials and combined into a unitary structure; and
  the material of the at least one feature is pliant and the material of the cap body is substantially rigid.

12. The detachable cap according to claim 11, wherein the canister has an exposed portion that is not covered by the inhaler housing, and wherein the at least one feature is engaged with the exposed portion by generating the tight fit between the detachable cap and the exposed portion of the canister for securing the cap thereto.

13. The detachable cap according to claim 12, wherein the cap body defines an internal surface, and wherein the at least one feature is arranged on the internal surface and fits over the exposed portion of the canister.

14. The detachable cap according to claim 11, wherein the at least one feature is configured as a projection.

15. The detachable cap according to claim 11, wherein the cap body is configured to glow in low light conditions.

16. The detachable cap according to claim 11, wherein the cap body includes a first portion arranged at the first end proximate to the actuation surface and a second portion arranged at the second end proximate to the at least one feature, and wherein the first portion is configured to remain exposed relative to the inhaler housing when the actuation surface is pressed by the user to dispense the aerosolized first substance and the second portion is configured to extend into the inhaler housing when the first substance is aerosolized.

17. The detachable cap according to claim 16, wherein the first portion is characterized by a distinct appearance of one of a fruit, a berry, a cartoon character, and a media character.

18. The detachable cap according to claim 11, wherein the cap body is impregnated with a second substance.

19. The detachable cap according to claim 18, wherein: the first substance includes a medication characterized by a distasteful scent; and
 the second substance is characterized by a scent configured to counteract the distasteful scent of the first substance.

20. The detachable cap according to claim 11, wherein the detachable cap includes a flexible middle section configured to accommodate relative movement between the canister and the inhaler housing when the detachable cap is secured to the canister and the inhaler housing.

* * * * *